United States Patent [19]
Brahms et al.

[11] Patent Number: 5,998,487
[45] Date of Patent: Dec. 7, 1999

[54] ANTI-INFLAMMATORY AND ANTIBACTERIAL BENZYL PHENOL AGENTS AND THEIR USE IN ORAL COMPOSITIONS

[75] Inventors: John C. Brahms, Piscataway; Dale S. Scherl, Somerset; Susan Herles, Flemington, all of N.J.; Stuart Shapiro, Kilchberg, Switzerland; Abdul Gaffar, Princeton, N.J.

[73] Assignee: Colgate-Palmolive Company, New York, N.Y.

[21] Appl. No.: 09/057,249

[22] Filed: Apr. 8, 1998

[51] Int. Cl.$^6$ .............. A61K 31/05; A61K 7/16
[52] U.S. Cl. .......... 514/736; 514/734; 514/731; 424/49
[58] Field of Search ............ 514/736, 734, 514/731

[56] References Cited

U.S. PATENT DOCUMENTS

| | | | |
|---|---|---|---|
| 3,928,624 | 12/1975 | Cragoe et al. | 424/330 |
| 4,244,956 | 1/1981 | Dewhirst | 424/258 |
| 4,563,526 | 1/1986 | Dewhirst | 546/152 |
| 5,188,821 | 2/1993 | Gaffar et al. | 424/52 |
| 5,192,531 | 3/1993 | Gaffar et al. | 424/52 |
| 5,512,561 | 4/1996 | Chandrakumar et al. | 514/11 |
| 5,677,296 | 10/1997 | Chrusciel et al. | 514/211 |
| 5,723,500 | 3/1998 | Stringer et al. | 514/736 |

FOREIGN PATENT DOCUMENTS 528 468 A1   2/1993   European Pat. Off. .

OTHER PUBLICATIONS

Offenbacher et al., *J. Periodont. Res.*, 21, 101–112 (1986).
Goodson et al., *Prostaglandins*, 19, 81–85 (1974).
Stralfors, *Archs. Oral* 12, 1375–1385 (1967).
Dewhirst, *Prostaglandins*, 20, No. 2, 209–222 (1980).
Offenbacher et al., *J. Periodon. Res.*, 19, 1–13 (1984).

*Primary Examiner*—Kevin E. Weddington
*Attorney, Agent, or Firm*—Henry S. Goldfine

[57] ABSTRACT

An antibacterial, anti-inflammatory compound for use in oral products, of the formulae:

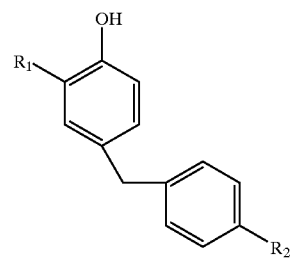

Wherein: $R_1$ and $R_2$ are straight chain or branched alkyl substituents or cycloalkyls with one or more alkyl substituents.

9 Claims, No Drawings

ANTI-INFLAMMATORY AND ANTIBACTERIAL BENZYL PHENOL AGENTS AND THEIR USE IN ORAL COMPOSITIONS

FIELD OF THE INVENTION

This invention relates to novel antibacterial and anti-inflammatory benzylphenol compounds, which compounds find useful application when used in oral compositions to provide enhanced antiplaque, antigingivitis and anti-periodontal disease benefits.

BACKGROUND OF THE INVENTION

Plaque bacteria generate toxins that cause oral diseases, including gingivitis and periodontal disease. Gingivitis is the initial stage of such disease, wherein the gums become red and puffy; the gums bleed when subjected to minor abrasion, as with toothbrushing; and there is persistent bad breath. Continued plaque invasion leads to periodontal disease, affecting the periodontium, which is the investing and supporting tissue surrounding a tooth (i.e. the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue.

Microorganisms contribute to both the initiation and progress of periodontal disease. These microorganisms, such as streptococcus mutans, colonize the pellicle film that surrounds each tooth, forming a soft mass. The plaque at and below the gingival margin, and the hard dental calculus that results from such plaque, causes gingivitis and subsequently periodontal pockets, pathologically deepened gingival sulcus. The body's immune response within such pockets, includes the synthesis of prostaglandins (PG), important immunoregulators, related to inflammatory response and the product of two enzyme isoforms, cyclooxygenase-1 (COX-1) and cyclooxygenase-2 (COX-2). COX-2 is induced by cytokines, mitogens and endotoxins in inflammatory cells and is responsible for the elevated production of PG and inflammation. Offenbacher et al., *J. Periodont Res.*, 21, 101–112 (1986) and Goodson et al., *Prostaglandins*, 19, 81–85 (1974) showed that extremely high levels of COX-2 are present within inflamed periodontal tissue, while COX-2 was low within such tissue in remission. The COX-2 level within active periodontal pockets approximates 1 $\mu$M (Offenbacher et al., *J. Periodon. Res.*, 19, 1–13 (1984)), a level believed to induce vasodilation, bone resorption and other pro-inflammatory responses. Accordingly, an agent having both anti-bacterial and PG inhibition properties is necessary to combat the bacterial formation of plaque and the associated gingivitis; and to inhibit the activity of COX-2, to reduce PG related inflammation and bone resorption associated with periodontal disease.

Since the 1860's, when Lister used phenol as a surgical antiseptic, it has been known that nearly all derivatives of phenol have some degree of bactericidal activity, when tested in tube dilution, disc agar, diffusion or similar assays. Dewhirst, in *Prostaglandins*, 20, No. 2, 209–222 (1980) examined sixty-three phenolic compounds for their ability to inhibit prostaglandin cyclooxygenase, as non-steroidal anti-inflammatory agents. Dewhirst reported that the most potent inhibitors possessing a two aromatic ring structure, connected by a short bridge, wherein one ring was apolar, the other ring contained a phenolic hydroxyl, ortho to the bridge, and the bridge contained a Lewis base such that the compounds could form bidentate metal chelates.

Three phenolic substances have been shown to inhibit caries in hamsters without adverse weight loss. Stralfors, *Archs. Oral*, 12, 1375–1385 (1967). The three phenolic substances were quercetin (pentahydroxyflavone), caffeic acid (3,4-dihydroxycinnamic acid) and protocatechuic acid (3,4-dihydroxybenzoic acid). Other phenolic substances are well know and widely used antimicrobials, such as thymol (2-isopropyl-5-methylphenol), which is found in commercial mouthrinse formulations. U.S. Pat. No. 5,723,500 discloses noncationic antibacterial alkylated phenol compounds for use in oral compositions which are antibacterial and provide antiplaque efficacy. U.S. Pat. No. 3,928,624 disclosed aminoethylphenols containing halogen and alkyl substituents as anti-inflammatory agents. U.S. Pat. Nos. 4,244,956 and 4,563,526 disclosed substituted 2-(arylmethoxy)phenol compounds, as medicinal agents which inhibit the synthesis of prostaglandins, inhibit platelet aggregation and are useful as topical and systemic anti-inflammatory agents. U.S. Pat. Nos. 5,512,561 and 5,677,296 disclose carbamic acid derivatives of substituted bibenzoxazepine compounds as analgesic agents for the treatment of pain, and prostaglandin-$E_2$ (COX-2) antagonists for the treatment of prostaglandin-$E_2$ mediated diseases. EP Patent Application 0 528 468 A1 discloses the use of triclosan (2',4,4'-trichloro-2-hydroxy-diphenyl-ether) for the inhibition and/or reduction of periodontitis, wherein triclosan inhibits cyclooxygenase activity and also reduces microbial challenge.

There is a continuing need in that art for more effective antibacterial agents compatible with anionic components in oral compositions which inhibit cyclooxygenase and PG activity; to combat plaque, gingivitis, and periodontal disease.

SUMMARY OF THE INVENTION

The present invention provides antibacterial, anti-inflammatory benzylphenol (AAB) compounds having the following structure, Formula I:

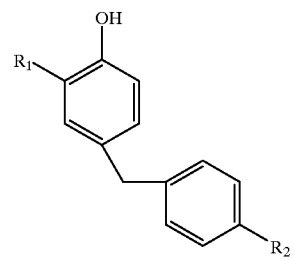

Wherein: $R_1$ and $R_2$ are straight chain or branched alkyl substituents or cycloalkyls with one or more alkyl substituents.

The term "alkyl" as used herein means a saturated hydrocarbon radical having from one to ten carbon atoms, and within which includes one to six carbon atoms, and further within which includes one, two, or three carbon atoms, which can be straight or branch chain. Representative of such radicals are methyl, ethyl, propyl, isopropyl, butyl, sec-butyl, isobutyl, tert-butyl, pentyl and the like.

The AAB compounds have particular application in oral compositions, comprising a therapeutically-effective amount of an AAB compound of Formula I, in combination with an orally acceptable vehicle; wherein, when such compositions are applied to oral surfaces there is provided enhanced antibacterial and anti-inflammatory benefits.

The AAB compounds are also useful for application in antibacterial personal care products, such as skin creams and lotions and household surface care products, where germ killing and reduction of skin irritation are desired.

DETAILED DESCRIPTION OF THE INVENTION

In one aspect, the present invention provides AAB compounds comprising the structure of Formula I, as described and defined above. A preferred embodiment of this invention is 2-t-butyl-4-(4-t-butylbenzyl)-phenol, whose structure is shown below as Formula II:

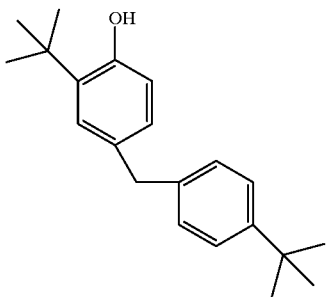

Compounds of the present invention, such as 2-t-butyl-4-(4-t-butylbenzyl)-phenol, exhibit activity as antibacterial agents and prostaglandin antagonists and as such would be useful in treating bacterial infections and PG mediated diseases.

Preparation of the preferred 2-t-butyl-4-(4-t-butylbenzyl)-phenol compound is representative of that of many of the compounds of the present invention, which are by means generally known in the art The preferred 2-t-butyl-4-(4-t-butylbenzyl)-phenol compound is prepared by the Friedal-Crafts alkylation of 4-benzylphenol (4-hydroxydiphenylmethane), available from Aldrich Chemical Company, Milwaukee, Wis., 53233. The Friedal-Crafts alkylation is a typical electrophilic aromatic substitution, in which, in the presence of a Lewis acid catalyst, such as aluminum chloride ($AlCl_3$), an alkyl halide is used to alkylate benzene to an alkylbenzene.

The AAB compounds of the present invention may be incorporated with other ingredients to form oral compositions, such compositions may be a solution of ingredients, such as a mouthwash; or a semisolid, such as a toothpaste or gel, which may contain 0 to 75% of a polishing agent; or a chewing gum; or a solid lozenge; or the like. In the use wherein the oral composition is a gel or paste dentifrice, a therapeutically-effective amount of the AAB compound of Formula I, is contained within a vehicle suitable for use in the oral cavity, which contains water, humectant, surfactant and a polishing agent or abrasive.

The humectant used in the preparation of a gel or paste dentifrice composition of the present invention is generally a mixture of humectants, such as glycerol, sorbitol and polyethylene glycol of a molecular weight in the range of 200–1,000, but other mixtures of humectants and single humectants may also be employed. The humectant content within the dentifrice is in the range of about 10 to about 30% by weight, and preferably about 10 to about 20% by weight. The water content is from about 30 to about 60% by weight, and preferably from about 40 to about 55% by weight.

As incorporated in the oral compositions of the present invention, an effective bactericidal and prostaglandin inhibiting, non-toxic amount of the AAB compound is typically in a range of about 0.003 to about 5%, preferably about 0.005 to about 3%, more preferably about 0.02 to about 1% by weight.

To enhance the antibacterial activity of the AAB compound, an antibacterial enhancing agent may be included in the oral composition. The use of such antibacterial enhancing agents in combination with water-insoluble noncationic antibacterial compounds is known to the art, as for example, U.S. Pat. Nos. 5,188,821 and 5,192,531.

Antibacterial enhancing agents preferred for use in the practice of the present invention include a natural or synthetic anionic polymeric polycarboxylate having a molecular weight of about 1,000 to about 5,000,000, preferably about 30,000 to about 500,000. Synthetic anionic polymeric polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, as Gantrez®, AN 139 (M.W. 500,000), AN 119 (M.W. 250,000); and preferably S-97 Pharmaceutical Grade (M.W. 700,000), from ISP Technologies, Inc., Bound Brook, N.J. 08805.

Other polymeric polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA® No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polyitaconic and polymaleic acids, and sulfonacrylic oligomers of M.W. as low as 1,000 available as Uniroyal® ND-2.

Also useful in the practice of the present invention are the so-called carboxyvinyl polymers, commercially available, for example, under the trademarks Carbopol® 934, 940 and 941 from B.F. Goodrich, Cleveland, Ohio 44131, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

The antibacterial enhancing agent, when employed, is incorporated in the compositions of the present invention in weight amounts of about 0.05 to about 5%, preferably about 0.1 to about 3%.

Linear molecularly dehydrated polyphosphate salts can be optionally employed herein as anticalculus agents. They are well known, being generally employed in the form of their wholly or partially neutralized water soluble alkali metal (e.g. potassium or preferably sodium) or ammonium salts, and any mixtures thereof. Representative examples include sodium tripolyphosphate, monosodium triacid,-, disodium diacid-, trisodium monoacid-, and tetrasodium-pyrophosphates, the corresponding potassium salts and the like. In the present invention, they can be employed in the oral compositions in approximate weight amounts of about 0.1 to about 3%, typically about 1 to about 2.5%, more typically about 1.5 to about 2%, especially about 2%. Particularly desirable anticalculus agents are tetraalkali metal pyrophosphates such as tetrasodium and tetrapotassium pyrophosphates, and mixtures thereof.

Fluoride ions may desirably also be included in the oral compositions of the present invention to provide an anticaries effect. Among these materials are inorganic fluoride salts, such as soluble alkali metal fluoride salts, for example, sodium fluoride, potassium fluoride, ammonium fluoride, sodium monofluorophosphate, and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

When the oral composition is substantially semi-solid or pasty in character, such as a toothpaste or gel, the dentifrice vehicle may contain a dentally acceptable abrasive material such as sodium bicarbonate, sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, and/or bentonite.

The abrasive material is generally present in the paste or gel composition in weight concentrations of about 0% to about 75% by weight, preferably about 0% to about 30% by weight in a gel and about 25% to about 60% by weight in a paste.

Toothpastes as well as gels typically contain a natural or synthetic thickener in proportions of about 0.1 to about 10% by weight, preferably about 0.5 to about 5% by weight. Suitable thickeners include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Surfactants are used in the compositions of the present invention to achieve increased prophylactic action and assist in achieving thorough and complete dispersion of the AAB compound throughout the oral cavity. The surfactant is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2- dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish teeth sensitivity such as potassium nitrate and potassium citrate can also be included in the oral compositions of the present invention at concentrations of about 0.1 about 10% by weight.

Various other materials may be incorporated in the oral compositions of this invention including whitening agents such as urea peroxide, hydrogen peroxide, preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the AAB compound is dispersed in a mixture of ingredients, e.g. alcohol, humectants, surfactants, and salts such as sodium fluoride and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The AAB compounds of this invention can be incorporated in lozenges, or in chewing gum or other products, e.g. by stirring into a warm gum base or coating the outer surface of a gum base, illustrative of which may be mentioned jelutone, rubber latex and vinylite resins desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrolysate hydrogenated glucose, hydrogenated disaccharides or hydrogenated polysaccharides, in an amount of about 90 to 98% by weight of the total composition. Salts such as sodium bicarbonate, sodium chloride, potassium bicarbonate or potassium chloride may totally or partially replace the polyol carrier. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, and aluminum stearate.

Lozenge formulations contain about 2% gum as a barrier agent to provide a shiny surface as opposed to a tablet which has a smooth finish. Suitable non-cariogenic gums include kappa carrageenan, carboxymethyl cellulose, and hydroxyethyl cellulose.

The following examples are illustrative of the compounds and use of such compounds of the present invention, but it is understood that the invention is not limited thereto. All amounts and proportions referred to herein and in the appended claims are by weight unless otherwise indicated.

EXAMPLE I

For the synthesis of 2-t-butyl-4-(4-t-butylbenzyl)-phenol of the present invention, 5.0 g of 4-benylphenol was weighted into a 100 ml 2-neck round bottom flask equipped with a magnetic stirrer and two gas inlet adapters. Using a syringe, 25.0 mL of an alkyl halide, 2-chloro-2-methylpropane, was added to the round bottom flask. The mixture was stirred at ambient room temperature for 5 minutes, until all of the 4-benzylphenol dissolved. The flask was placed in an ambient (22° C.) temperature cooling bath and 1.0 g the catalyst, $AlCl_3$, was added in small amounts over the course of 5 minutes. Once gas evolution subsided, the mixture was stirred at room temperature for 15 minutes. The product was purified using silica gel column chromatograph, with an eluent of 3% ethyl acetate and 97% hexane. An 83% yield, 6.7 g, of purified 2-t-butyl-4-(4-t-butylbenzyl)-phenol product of was isolated as a yellow oil.

EXAMPLE II

The efficacy of the AAB compounds of the present invention as prostaglandin (inflammation) inhibitors was demonstrated using an assay involving, production of prostaglandin $E_2$ ($PGE_2$) in cultures of human cells stimulated by the cytokine IL-1β, with varying levels of 2-t-butyl-4-(4-t-butylbenzyl)-phenol an AAB compound of the present invention. Specifically, Human Embryo Palatal Mesenchyme cells (HEPM, ATCC #1486) cells were grown in high glycose Delbeco's Modified Eagles Medium (DMEM, Gibco/BRL-Life Technologies, Grand Island, N.Y.) containing 10% heat inactivated fetal bovine serum (FBS, Gibco/BRL). The cells were grown at 37° C., 100% humidity, and 10% $CO_2$. Prior to analysis, the cells were subcultured into 24 well plates, to form 12 sets of duplicate cultures, and allowed to become 70–90% confluent. On day one of the experiment, the cells were washed three times with serum free media (containing 0.5% bovine serum albumin, BSA), followed by replacement with BSA containing media alone (the negative control) in the first culture set; media and 1.0 ng/mL IL-1β (the positive control, without any inhibitor) in the second culture set; and media, 1.0 ng/mL IL-1β, and a range of from 0.01 μM to 50 μM of 2-t-butyl-4-(4-t-butylbenzyl)-phenol in the third thru twelfth culture sets. Exposure was for 24 hours at which time the media was removed from each well, the media's pH was adjusted to 3.5 with HCl, and the media was analyzed for $PGE_2$ produced using a PerSeptive Diagnostics TiterFluor $PGE_2$ EIA kit, available from PerSeptive Biosystems, Framingham, Mass. 01701.

Prior to determining the $PGE_2$ inhibitory effect of the 2-t-butyl-4-(4-t-butylbenzyl)-phenol compound of the present invention, the results must be normalized with respect to the number of viable cells in each culture well; more or less cells producing correspondingly more or less $PGE_2$. A modified MTT assay was used to determine the number of cells in each culture well. After removal of the original media for the $PGE_2$ determination, the cells within each culture well were then washed two times with media containing serum (growth media) and each culture well was refilled with 1.0 ml growth media containing 0.5 mg MTT reagent (Sigma Research, St. Lois, Mo. 63178). After 3 hours, at 37° C., the media was decanted off and 1.0 ml of 0.04N HCl in isopropanol was used to dissolve the purple formazan crystals which had formed. Once dissolved, the spectroscopic absorbance of 100 μl of the isopropanol solution from each culture well was determined at 570 nm. A normalization factor, the cell concentration ratio, was calculated for each culture well, by dividing the absorbance of the particular culture well's isopropanol solution by the average absorbance of the unstimulated negative control set's isopropanol solutions. The $PGE_2$ originally determined for each culture well was then normalized by being mutiplying by the cell concentration ratio calculated for that particular culture well. The normalized $PGE_2$ results of each culture set were compared to the $PGE_2$ concentration of the stimulated positive control set, containing no 2-t-butyl-4-(4-t-butylbenzyl)-phenol inhibitor, to determine the degree of inhibition of stimulated $PGE_2$ production within each culture set. Knowing the normalized percentage prostaglandin inhibition of the various concentrations of 2-t-butyl-4-(4-t-butylbenzyl)-phenol, the concentration of 2-t-butyl-4-(4-t-butylbenzyl)-phenol necessary to inhibit 50% of the positive control, the the $IC_{50}$, was calculated. The calculated $PGE_2$ $IC_{50}$ of 2-t-butyl-4-(4-t-butylbenzyl)-phenol is recorded in Table I, below.

For comparison, the $PGE_2$ $IC_{50}$ assay methodology of Example II was repeated using the known $PGE_2$ inhibitor triclosan. The result of this comparative assay has also been recorded in Table I.

TABLE I

| Inhibition of $PGE_2$ Assay | |
| --- | --- |
| Compound | $IC_{50}$ Concentration to Inhibit 50% of $PGE_2$ (μMolar) |
| Triclosan | 7.0 |
| 2-t-butyl-4-(4-t-butylbenzyl)phenol | 3.7 |

Referring to Table I, 2-t-butyl-4-(4-t-butylbenzyl)-phenol, a compound of the present invention is shown to be significantly, almost 2 times, more efficacious as a $PGE_2$ inhibitor than triclosan.

EXAMPLE III

The efficacy of the AAB compounds of the present invention as inhibitors of COX-1 and COX-2 enzymes was shown using the oxygen utilization assay described in Dewhirst, *Prostaglandins*, 22, 209–222 (1980). Varying concentrations of 2-t-butyl-4-(4-t-butylbenzyl)-phenol, a compound of the present invention were selected that inhibit the enzymatic activity from 20% to about 80%, as compared to a positive control, no inhibitor. These varying concentrations of 2-t-butyl-4-(4-t-butylbenzyl)-phenol were independently added to COX-1 and COX-2 enzymes in a closed system, in which the enzymes were reacted in a reaction requiring molecular oxygen. The degree of inhibition of the COX enzyme activity was measured by the reduction in monitored oxygen consumption as a function of time within the closed system. The COX enzyme $IC_{50}$, concentration of 2-t-butyl-4-(4-t-butylbenzyl)-phenol found to inhibit 50% of the activity of the COX-1 and COX-2 enzymes is recorded in Table II.

For comparison, the COX enzyme $IC_{50}$ assay methodology of Example III was repeated using triclosan, an agent known to inhibit PG by inhibiting the production of its COX-1 and COX-2 precursors. The results of this comparative assay has also been recorded in Table II.

TABLE II

Inhibition of COX-1 and COX-2 Assays

| Compound | $IC_{50}$ Conc. to Inhibit 50% of COX-1 Activity ($\mu$Molar) | $IC_{50}$ Conc. to Inhibit 50% of COX-2 Activity ($\mu$Molar) |
|---|---|---|
| Triclosan | 43.0 | 229.5 |
| 2-t-butyl-4-(4-t-butylbenzyl)-phenol | 17.4 | 100.0 |

The results recorded in Table II demonstrate that 2-t-butyl-4-(4-t-butylbenzyl)-phenol, a compound of the present invention, is a significantly, over 2 times more efficacious, COX-1 and COX-2 inhibitor than triclosan.

EXAMPLE IV

The antibacterial efficacy of 2-t-butyl-4-(4-t-butylbenzyl)-phenol, a AAB compound of the present invention, was evaluated in accordance with a MIC (Minimum Inhibitory Concentration) test which measures the minimum concentration in ppm of the 2-t-butyl-4-(4-t-butylbenzyl)-phenol at which the growth of bacteria is completely inhibited. The smaller the MIC, the greater the antibacterial activity of the compound being tested.

Using a 96 well microtiter plate, a 100 $\mu$l of trypticase soy broth (TSB) media, available from BBL, Cockeysville, Md. 21030, was placed in each of the 12 columns within the plate. Using a octapette pipettor, the 2-t-butyl-4-(4-t-butylbenzyl)-phenol compound was serially diluted to each of the 12 columns, from 125 ppm in the first well of each column, to 0.061 ppm in the $12^{th}$ (each column containing ½ the concentration of 2-t-butyl-4-(4-t-butylbenzyl)-phenol compound than the previous column). To each of the 12 columns an additional 100 $\mu$l of TBS was added containing A. viscosus bacterium, a common oral bacteria, at a concentration optical density of 0.1, at 610 nm. The plate was then sealed and incubated for 24 hours at 37° C. The optical density of each column was read using a Bio-Tech Industries, Inc., Model $El_x$ 808 Microtiter Plate Reader, to determine quantity of bacteria present; the column containing the lowest concentration of 2-t-butyl-4-(4t-butylbenzyl)-phenol compound observed to inhibit the bacteria's growth, was designated the MIC and recorded in Table III, below.

The procedure of Example IV was simultaneously run with water as a negative control and using a known efficacious antibacterial agent, triclosan, as a comparative and positive control. The MIC determined for the triclosan is also recorded in Table III for comparative purposes.

TABLE III

Bacterial Minimum Inhibitory Concentration

| Compound | MIC (ppm) |
|---|---|
| Triclosan | 3.61 |
| 2-t-butyl-4-(4-t-butylbenzyl)-phenol | 0.24 |

Referring to Table III, as shown the MIC of the AAB 2-t-butyl-4-(4-t-butylbenzyl)-phenol compound of the present invention, is significantly only about 7% that of triclosan.

EXAMPLE V

To demonstrate the compatibility of the AAB compounds of the present invention with typical dentifrice ingredients, a liquid dentifrice of the following formula was prepared:

TABLE IV

| Ingredients | Composition (grams) |
|---|---|
| Phase I | |
| Distilled Water | 56.46 |
| Sodium Fluoride | 0.24 |
| Sorbitol | 20.0 |
| Phase II | |
| Propylene Glycol | 0.50 |
| Glycerol | 20.0 |
| Phase III | |
| Flavor | 1.0 |
| 2-t-butyl-4-(4-t-butylbenzyl)-phenol | 0.30 |
| Phase IV | |
| Sodium Lauryl Sulfate | 1.5 |

In the preparation of the liquid dentifrice, the ingredients for Phase I were weighted into a 4 oz. jar equipped with a magnetic stirrer and stirred at room temperature, with moderate agitation, for 5 minutes. The ingredients for Phase II were combined in a 50 mL beaker equipped with a magnetic stirrer and stirred for 5 minutes. Phase II was added to Phase I with stirring and the mixture was stirred for 5 minutes. Phase III ingredients were combined in a small screw cap vial, capped and shaken vigorously by hand until homogeneous. Phase III was added to the combined Phase I and II mixture and the combination stirred for 10 minutes. Phase IV was weighted onto a piece of weighing paper and added to the combination of Phases I, II and III, in small aliquots over the course of 5 minutes while stirring. The final combination of Phases I, II, III and IV was stirred at room temperature for 1 hour, resulting in a stable, consumer acceptable liquid dentifrice.

What is claimed is:

1. An antibacterial compound having anti-inflammatory prostaglandin inhibitory properties and having the structural formula:

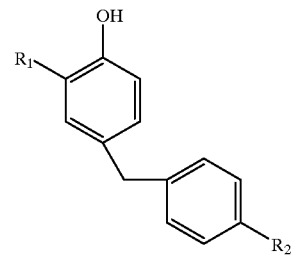

Wherein: $R_1$ and $R_2$ are straight chain or branched alkyl substituents or cycloalkyls with one or more alkyl substituents.

2. A compound according to claim 1, which compound is 2-t-butyl-4-(4-t-butylbenzyl)-phenol.

3. An antiplaque oral composition comprising an orally acceptable vehicle and an effective antibacterial, anti-inflammatory amount of a compound of the formulae:

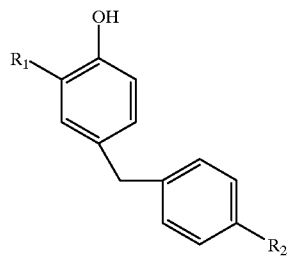

Wherein: $R_1$ and $R_2$ are straight chain or branched alkyl substituents or cycloalkyls with one or more alkyl substituents.

4. A composition according to claim 3, wherein the compound is 2-t-butyl-4-(4-t-butylbenzyl)-phenol.

5. The composition of claim 3, wherein the compound is present in the oral composition in an amount ranging from about 0.003 to about 5% by weight.

6. The composition of claim 3, wherein an anionic polycarboxylate antibacterial enhancing agent is incorporated in the composition.

7. A composition according to claim 3, wherein the composition is in the form of a mouthrinse.

8. A composition according to claim 3, wherein the composition is in the form of a dentifrice containing a polishing agent and a vehicle of water and a humectant.

9. A method of promoting oral hygiene comprising applying to oral surfaces an effective amount of a composition as defined in claim 3.

* * * * *